US00PP09443P

United States Patent [19]

Twomey

[11] Patent Number: Plant 9,443

[45] Date of Patent: Jan. 30, 1996

[54] HYBRID TEA ROSE PLANT NAMED TWOHONOR

[75] Inventor: Jerry Twomey, Leucadia, Calif.

[73] Assignee: DeVor Nurseries, Inc., Freedom, Calif.

[21] Appl. No.: 153,454

[22] Filed: Nov. 15, 1993

(Under 37 CFR 1.47)

[51] Int. Cl.[6] ..... A01H 5/00

[52] U.S. Cl. ..... Plt./18

[58] Field of Search ..... Plt./11, 18, 19

*Primary Examiner*—Howard J. Locker

*Attorney, Agent, or Firm*—Christie, Parker & Hale

[57] ABSTRACT

A new Hybrid Tea rose plant producing ivory pink flowers.

1 Drawing Sheet

SUMMARY OF THE INVENTION

The present invention relates to a new and distinct variety of rose plant of the Hybrid Tea rose class which was originated by my crossing as seed parent the variety known as 'Sheer Elegance' and as pollen parent an unnamed, unpatented seedling of my creation. The varietal denomination of this new rose is 'Twohonor'.

Among the novel characteristics possessed by this new variety which distinguish it from its parents and all other varieties of which I am aware are its attractive medium pink flowers fading to paler yellow-tone pink at its center borne on a plant with attractive semi-glossy foliage. The new variety differs from its parent 'Sheer Elegance' in flower coloration. Whereas 'Sheer Elegance' is of neyron rose to rhodonite red coloration, the new variety has a generally lighter and pinker coloration, with a decidedly yellow cast at its center. 'Twohonor' is also more resistant to blackspot than its parent.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DETAILED DESCRIPTION OF THE NEW VARIETY

Parentage: Seedling.

*Seed parent.*—'Sheer Elegance'.

*Pollen parent.*—Unnamed seedling.

Class: Hybrid Tea.

The following is a detailed description of my new variety, of specimens grown under glass in Watsonville, Calif. in the months of April–October. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Continuous.

A. Bud:

(1) *Size.*—Medium.

(2) *Form.*—Pointed.

(3) *Color.*—When sepals first divide, bud color is near 50A to 53C.

(4) *Sepals.*—Sepals cover bud when tight then spread upon opening of bud, after which they reflex. Color: When covering bud tightly, outer sepals are near 144B at base and tips are near 175B. Upon opening of bud, sepals spread and when divided, the base bottom remains near 144B and top ¾ of outer sepal becomes near 175A. Sepals reflex upon opening of the flower, and when fully reflexed are near 139D on inside of sepal.

(5) *Peduncle.*—Length: About 6.5–8.5 cm. Aspect: Straight with some occasional curving. Strength: Erect, sturdy. Color: Strip of near 144A, otherwise near 186B.

(6) *Bracts.*—Two, near 144B tinged with near 184D, broadly lanceolate with caudate apex.

B. Bloom:

(1) *Size.*—Average size when fully expanded — about 12 cm.

(2) *Borne.*—Singly, one to a stem.

(3) *Form.*—Pointed, imbricated, becoming slightly ruffled at maturity.

(4) *Petalage.*—Number of petals under normal conditions — about 48 to 52.

(5) *Color (⅓ to ½ open).*—Outer petals: Top surface: underlying color from center throughout top is near 65D; the very top of outer surface is veined with near 63C; center near 65D; bottom of base is near 1C darkening to near 13B towards center. Undersurface: near 65C; with veining of near 63C; veining gets more pronounced as it reaches outer edges. Center: near 65C; top of base is near 165C and bottom of base is near 1C. Inner petals: Top surface: near 65D with some veining of near 55B near edge; center of petal near 65D but heavily veined with near 22B; base near 19B with tip of base near 2A; center near 65C and base near 165C with top of base near 1C. The base of petals at point of attachment is near 150C and the general tonality from a distance is medium pink.

(6) *Color (fully open).*—Outer petals: Top surface: Outer surface: outer edge of petals near 56C with heavy veining of 64D. Undersurface base is near 62D with veining of near 63D at top edges. Inner petals: Top surface is near 49D; center near 49D veined with near 22D and base near 10D; undersurface near 49C and base near 10D; petals at point of attachment are near 9A and the general tonality from a distance is pink blend.

(7) *Color change.*—As bloom ages the inner petals lighten to a very pale pink but veining of outer petals gives a darkening effect. Petal top surface between 56C to 56D; petal undersurface near 62D and general tonality at a distance is a more intense pink blend.

C. Petals:
(1) *Texture.*—Thick.
(2) *Appearance.*—Both inside and out are a dull finish.
(3) *Form.*—Slightly ruffled.
(4) *Arrangement.*—Imbricated.
(5) *Petaloids.*—Usually 5 to 6.
(6) *Fragrance.*—Slight old rose.
(7) *Lasting quality.*—Long lasting on plant and as cut flower; petals drop off cleanly on spent blooms.
(8) *Persistence.*—Petals drop.

REPRODUCTIVE ORGANS

A. Stamens:
(1) *Arrangement.*—Irregular, near 6D.
(2) *Anthers.*—Color — near 8B.
(3) *Filaments.*—Color — near 6D.
(4) *Pollen.*—Color — near 36A.

B. Pistils
(1) *Styles.*—Bunched, uneven.
(2) *Stigmas.*—Color — near 38D.

C. Characteristics of hips: Not observed.

PLANT

A. Form: Upright, compact.

B. Growth: Vigorous, hardy plant; height attained about 122 cm at first season.

C. Foliage: Compound 3, 5 and 7 leaflets.
(1) *Size.*—Medium.
(2) *Quantity.*—Abundant.
(3) *Color.*—New foliage: Upper side near 147A with bronzing effect near 175A on outer edges, most notably on top and somewhat visible on remaining leaves of leaflet. Underside is near 147B. Old foliage: Upper side — near 147A. Under side — near 147B.
(4) *Shape.*—Ovate.
(5) *Texture.*—Semi-glossy.
(6) *Edge.*—Serrate.
(7) *Serration.*—Denticulate.
(8) *Leaf stem.*—Color — medium green.
(9) *Stipules.*—Medium, slender, slightly bearded.
(10) *Rachis.*—Small prickles.
(11) *Petioles.*—Top near 184B; underside near 144D.
(12) *Auricle.*—Long, pointed, curving outward.
(13) *Resistance to disease.*—Moderate to blackspot; good to mildew; good to rust.

D. Wood
(1) *New wood.*—Color — new shoots near 183B. Bark — smooth.
(2) *Old Wood.*—Color — near 144A. Bark — rough.

E. Flower stem: About 41–53 cm from last cut.

F. Thorns:
*Quantity (main stalk).*—Ordinary.
*On laterals from stalk.*—Ordinary.
*Form.*—Slightly curved downward, thin.
*Length.*—Medium.
*Color.*—Near 152A when young with tinges of near 185D at base and throughout.
*Position.*—Irregular.
*Prickles.*—Profuse.

F. Winter hardiness: Moderately winter-hardy.

I claim:

1. A new and distinct variety of rose plant of the Hybrid Tea rose class, substantially as shown and described.

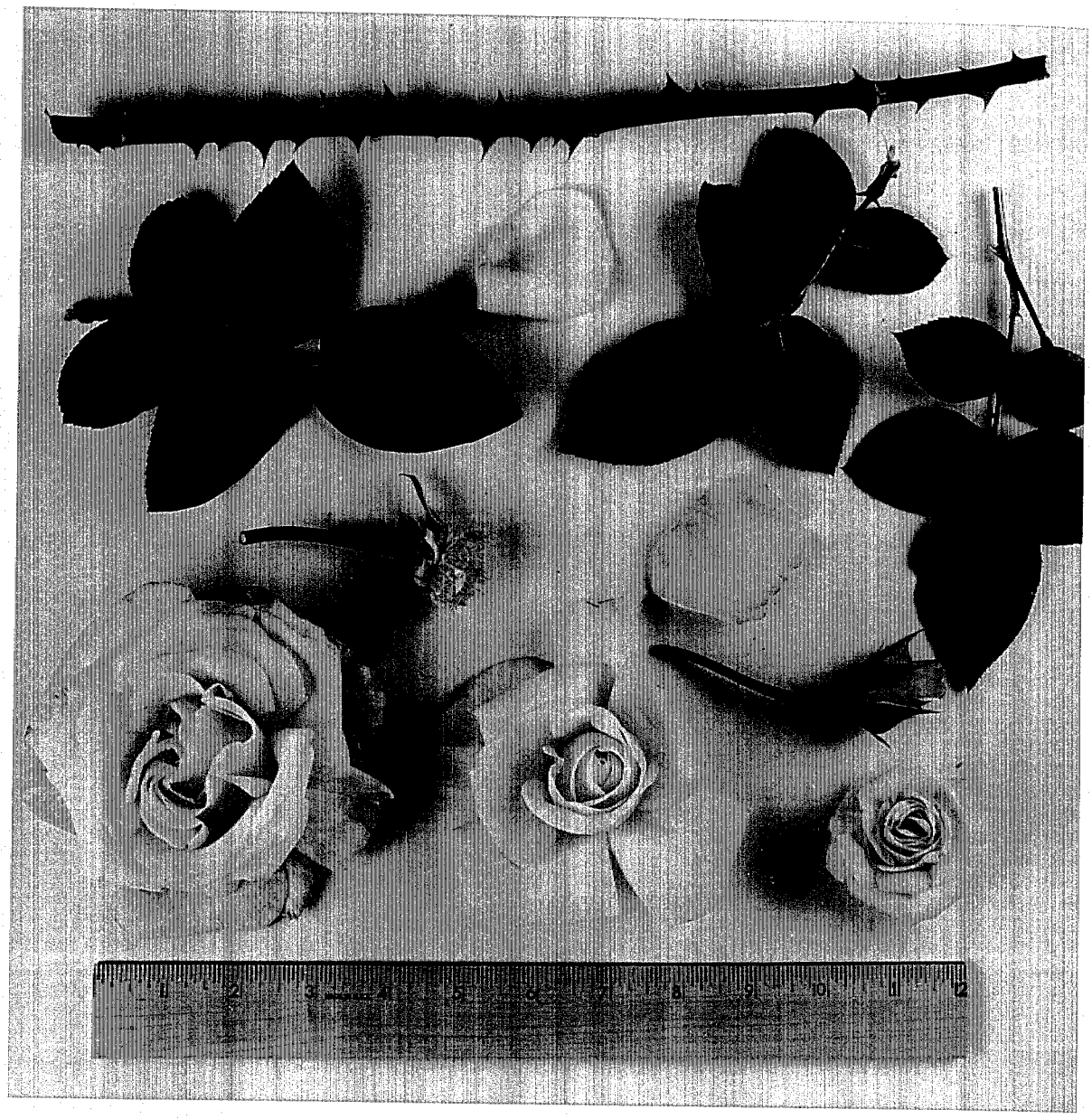

* * * * *